United States Patent [19]

Cason, Jr.

[11] 4,441,244

[45] Apr. 10, 1984

[54] SEALED BEARING ROTARY ROCK BIT ASSEMBLY

[75] Inventor: George A. Cason, Jr., Dallas, Tex.

[73] Assignee: Dresser Industries, Inc., Dallas, Tex.

[21] Appl. No.: 316,179

[22] Filed: Oct. 29, 1981

[51] Int. Cl.³ ............................................. B23P 19/04
[52] U.S. Cl. ...................................... 29/434; 29/460; 73/73
[58] Field of Search ..................... 73/73, 29; 184/1 E, 184/1 C; 34/15; 29/434, 460

[56] References Cited

U.S. PATENT DOCUMENTS

| | | | |
|---|---|---|---|
| 3,552,187 | 1/1971 | Groninger | 73/29 |
| 4,014,595 | 3/1977 | Dolezal | 308/8.2 |
| 4,172,477 | 10/1979 | Reich | 141/8 |
| 4,199,856 | 4/1980 | Farrow | 29/460 |

OTHER PUBLICATIONS

W.-K. R. Chia, "Preheat Temperature for Vacuum Dewatering of Sealed Bit Bearing Prior to Greasing"; ASME Paper 78-Pet-38, 11/5/78, pp. 1, 2, 8, and 9.
Hughes Tool Company advertisement World Oil, Aug. 1, 1976, p. 49, "New Vacuum/Pressure Greasing Method Adds to Performance of Sealed Bearing Bits" Product Catalog 1979; Precision Humidity Measurement and Calibration Equipment—*Thunder Scientific Corporation*, Albuquerque, New Mexico 87123.

*Primary Examiner*—E. Robert Kazenske
*Assistant Examiner*—Denis E. Corr
*Attorney, Agent, or Firm*—Fred A. Winans

[57] ABSTRACT

A water detecting system for detecting water in the bearings and lubricant reservoir system of a sealed bearing rotary rock bit permits detection and removal of water to decrease premature bearing failure caused by the presence of water on the bearing surface.

4 Claims, 1 Drawing Figure

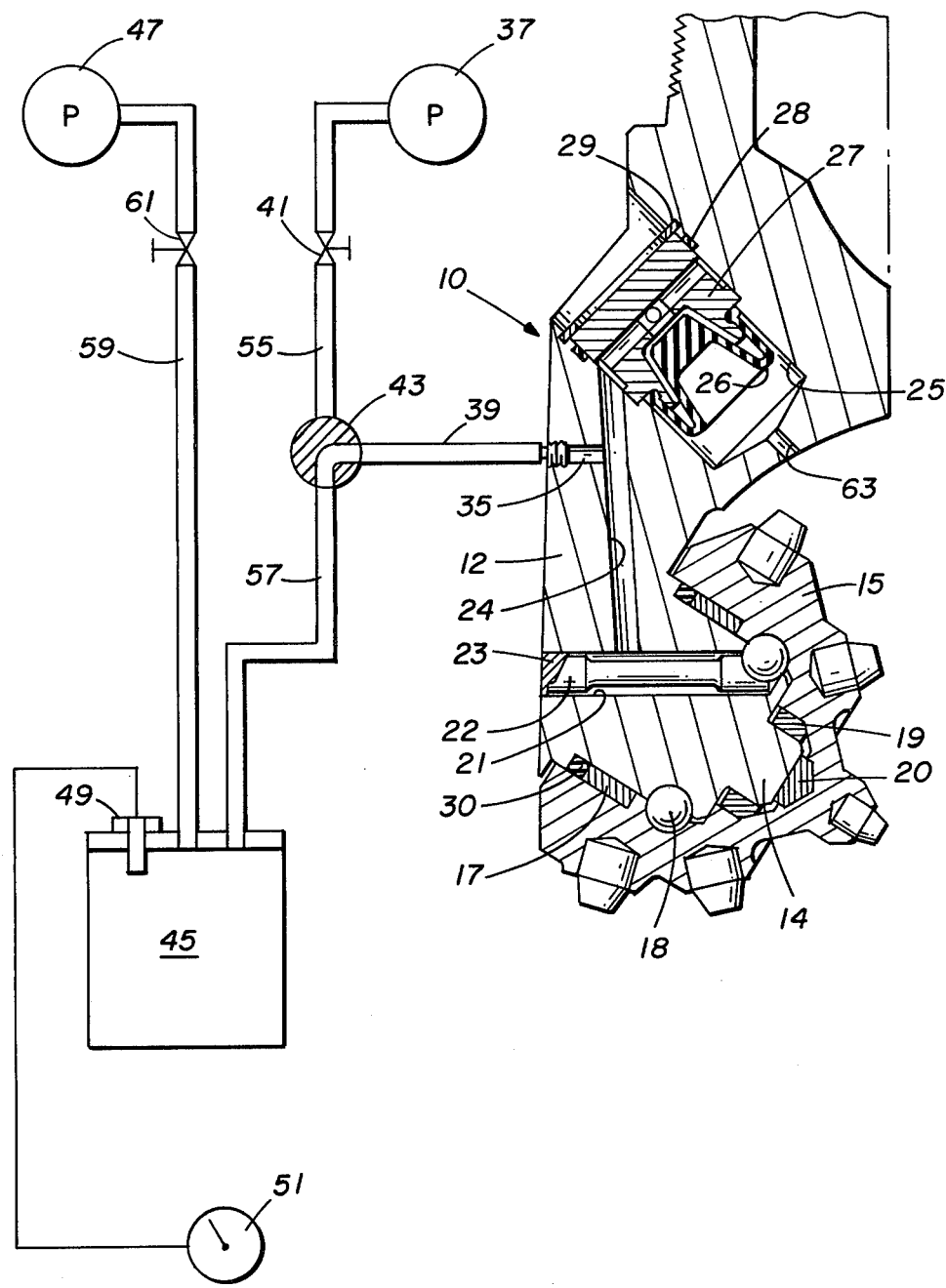

SEALED BEARING ROTARY ROCK BIT ASSEMBLY

BACKGROUND OF THE INVENTION

1. Field of the Invention

The present invention relates to the art of manufacturing a sealed bearing rotary rock bit in general and, more particularly, to a method of determining the presence of water in the bearings and lubricant system of a sealed bearing rotary rock bit.

2. Description of the Prior Art

While drilling a borehole in search of oil or gas, extreme environmental conditions are encountered. The borehole may contain drilling mud which is used for carrying the rock cuttings out of the bottom of the borehole, as well as to provide cooling to some extent for the rock bit (as the bore hole depth increases, the temperature may increase as much as 2 degrees per hundred foot of depth so that temperatures of 300 to 350 degrees or higher are often encountered by the rock bit). The weight of the drill string is set on the rock bit to aid in penetrating the formations and may vary from 10,000 to 80,000 lbs. or higher. Rotary speeds of the rock bit may vary from 20 rpm to as high as 250 rpm; however, 50 to 70 rpm is most likely to be used.

During the assembly of a sealed bearing rotary rock bit, it is possible for water to enter the bearing and lubricant system on several occasions; for example:

An O-ring seal is assembled onto the arm and smear grease is placed on the bearing surfaces and the O-ring surfaces. The cone is then assembled onto the arm and ball bearings are inserted into the ball race through the ball plug hole. A ball plug is then inserted to retain the balls in the ball race. The ball plug is then welded and the arm and cone assembly submerged in water to cool the weld on the ball plug and arm. The weld is pressure tested under water.

Three arms and cone assemblies are assembled together and welded into a rock bit, after which the tool joint or pin area is heated to anneal the weld affected pin material before being threaded. During this time the lower section of the bit containing the bearings and seals is submerged in water to protect the seal and bearings from the heat. The tool joint is then threaded during which time a coolant at a high pressure is sprayed over the thread cutting tool and surface being threaded with much coolant spray impinging on other parts of the rock bit.

After threading the pin end of the bit, the nozzle bores leading from the central passageway are plugged using solid plugs with O-rings. The bit is then inverted and the threaded end pressed against a gasket using a pneumatic ram to force the gasket to seal the opening at the threaded end. An air line permits pressurizing the central passageway of the bit and the bit submerged in water to check for leaks along the weld which, if present, are repaired.

Thus, it is evident that the bit is time and again subjected to conditions that could introduce water into the lubricant system and bearings. A small amount of water present in the lubricant on the bearing surfaces will reduce the lubricating properties of the lubricant causing premature failure of the rock bit bearings. Heretofore, there was no step for detecting the presence of water in the bearing system and lubricant system during bit assembly.

SUMMARY OF THE INVENTION

The present invention provides a method that will effectively reduce or eliminate infant mortality of sealed bearing rotary rock bit bearings caused by the presence of water in the lubricant system and bearing surfaces within the rock bit. The moisture detecting method of the present invention includes vacuum pumps to evacuate the air from the bearing cavity and lubricant system. A moisture detecting means provides a humidity sensor connected to a meter which will show the presence of humidity in the air being withdrawn from the bearing systems and lubricant system. If moisture is detected, some drying step is initiated, after which a similar test is again made until an acceptably dry system is indicated.

The above and other features and advantages of the present invention will become apparent upon consideration of the following detailed description of the invention when taken in conjunction with the accompanying drawing.

BRIEF DESCRIPTION OF THE DRAWING

The FIGURE is an illustration, partially in section, of one arm of a sealed bearing rotary rock bit with a schematic view of a preferred embodiment of an air evacuation and humidity sensing arrangement according to the invention.

DESCRIPTION OF THE PREFERRED EMBODIMENT

Referring now to the FIGURE, a sectional view of one arm 12 of a lubricated sealed bearing rotary rock bit is shown. The bearing system includes a plurality of bearings located between the rotatable cutter 15 and the stationary bearing pin 14 and include an outer friction bearing 17, a series of ball bearings 18 in opposed races, a friction bearing 19, and a thrust button 20.

The lubrication system of bit 10 includes a passage 24 that extends through the arm 12 to bearing pin 14 to allow lubricant to be transmitted to the bearing systems. A passage 21 connected to passage 24 allows the make-up of the ball bearing system 18 by allowing the balls to be inserted into position between the races after the cone cutter 15 is placed on the bearing pin 14. The series of ball bearings 18 serve to lock the cone cutter 15 on the bearing pin 14. After the balls are in place, a plug 22 is inserted into the bore 21 and welded therein by a weld 23. Plug 22 has a reduced diameter throughout the major portion of its length to allow lubricant to be transmitted to the bearing area. Additional passages may extend from bore 21 to the bearing area to insure a sufficient supply of lubricant to bearings 17, 18, 19 and 20.

A lubricant reservoir is located in the bit 10 to provide a supply of lubricant to the bearings. A flexible diaphragm 26 is positioned in a bore 25 and in cooperation with cap 27 encloses the reservoir to retain a supply of lubricant. The upper end of the lubricant reservoir is closed by a cap 27 locked in place by a snap ring 29. An O-ring seal 28 is positioned around the cap 27 to retain lubricant in the lubricant reservoir.

A seal 30 is located between the surface of the bearing pin 14 in the cone mouth of the cone cutter 15. The seal 30 retains the lubricant within the bit 10 and prevents the ingress of material in the borehole into the bearing system.

To the left of bit arm 12 is a schematic diagram of a moisture detecting circuit, which, in the preferred form, is applied subsequent to installing the flexible diaphragm 26 and cap 27 in the bore 25 and prior to injecting the lubricant thereinto; but which may be utilized at any appropriate position during the assembly of such a bit 10. I prefer to test for the presence of water in a sealed bearing rotary rock bit 10 as follows: first a tube 39 is attached to the grease filler hole 35 and the air is evacuated from the bearing system and lubrication system, by means of a vacuum pump 37, which evacuates the air to an initial vacuum through tube 55, three-way valve 43, and valve 41 located in tube 55. Cut-off valve 41 is then closed and three-way valve 43 is switched to connect the bearing system and lubrication system through tube 57 to the vacuum chamber 45. The vacuum chamber 45 was previously evacuated to a lower pressure (i.e. greater vacuum) than has been placed on the bearing system and lubrication system. The lower pressure in chamber 45 is obtained by attaching the chamber 45 to vacuum pump 47 by tube 59 and pulling a vacuum by vacuum pump 47 after which cut-off valve 61 located in tube 59 is closed. After switching three-way valve 43, the lower pressure in chamber 45 will draw a gas sample out of the bearing system and lubrication system into chamber 45. Any water vapor present in the gas sample pulled into the chamber 45 from the bearing system and seal lubrication system, will raise the relative humidity in chamber 45 by an amount proportional to the amount of water vapor present in the sample. Humidity sensor 49 (of a type readily commercially available such as humidity sensor model BR-101B from the Thunder Scientific Corporation, Albuquerque, New Mexico as described in their 1979 Product Catalog) in chamber 45 will detect the difference in the relative humidity in chamber 45 after the gas sample from the bearing system and lubrication system has been pulled into chamber 45. The change in the relative humidity in the chamber 45 will cause a change in the signal output of humidity sensor 49 going to meter 51 causing a change in the meter reading.

In my tests, I use arms from sealed bearing rotary rock bits having a bearing system and a lubricant system capacity of approximately 50 cubic centimeters and have used a chamber 45 of approximately 4900 cubic centimeters for housing the humidity sensor 49. Also, I have evacuated the bearing system and lubricant system to an initial vacuum of 70–125 mm of mercury and the vacuum chamber 45 to on the order of 10 mm of mercury. In arms having an acceptable moisture content, the change in the relative humidity reading due to the gas evacuated from the bit into vacuum chamber 45 would be approximately 1% to 1.6%. Arms that yielded a change in the relative humidity reading of greater than 1.6% could be dried by any drying procedure such as by attaching the arm to a vacuum pump for a period of time to vaporize the water in the systems. Subsequently the bit could be retested for an acceptable humidity level in accordance with the previous procedure. This procedure could be repeated until an acceptable moisture level was indicated at which time lubricant would be injected into the system.

Another method for testing for water in the bearing system and lubricant system employing a single vacuum pump, such as pump 47, attaching tube 39 to the grease filler hole 35 and evacuating the air from the bearing systems and lubricant system by pulling a vacuum directly through tube 39 and valve 43 and tube 57 into chamber 45. Humidity sensor 49 causes a reading on meter 51 which indicates the humidity in the gases evacuated from the bit. If an unacceptable humidity level is found in arm 10, the vacuum can be continued until an acceptable reading on meter 51 is obtained.

The embodiments of the invention in which an exclusive property or privilege is claimed are defined as follows:

1. A method of manufacturing a sealed bearing rotary rock bit comprising the steps of:
   assembling a seal and cone on a bearing pin of a rock bit arm;
   locking the cone and pin together with a retaining means so that the cone may rotate about the axis of the pin on cooperating engaging bearing structure forming a sealed bearing system;
   evacuating gases from said sealed bearing system to an initial pressure;
   evacuating a vacuum chamber to a pressure lower than said initial pressure and measuring the relative humidity therein to define an initial relative humidity;
   ducting said sealed bearing system to said vacuum chamber to evacuate additional gases from said system into said chamber and measuring the relative humidity of gases therein to define a resultant relative humidity; and
   injecting lubricant into said bearing system upon said resultant relative humidity being at or less than a maximum accepted value greater than said initial relative humidity.

2. A method of manufacturing a sealed bearing rotary rock bit comprising the steps of:
   assembling a seal and cone on a bearing pin of a rock bit arm;
   locking the cone and pin together with a retaining means so that the cone may rotate about the axis of the pin on cooperating engaging bearing structure forming a sealed bearing system;
   providing a sealed reservoir in said arm in fluid flow communication with said sealed bearing system;
   evacuating gases from said sealed bearing system and said reservoir to an initial pressure;
   evacuating a vacuum chamber to a pressure lower than said initial pressure and measuring the relative humidity therein to define an initial relative humidity;
   ducting said system and reservoir to said vacuum chamber to evacuate additional gases from said system and reservoir and measuring the relative humidity of gases therein to define a resultant relative humidity; and
   injecting lubricant into said bearing system and reservoir upon said resultant relative humidity being at or less than a maximum accepted value greater than said initial relative humidity.

3. A method according to either claim 1 or 2 wherein said maximum accepted value of said resultant relative humidity greater than said initial relative humidity is on the order of 1.6%.

4. A method according to claim 3 wherein said initial pressure is generally within the range of 70 to 125 mm of mercury and said lower pressure of said vacuum chamber is on the order of 10 mm of mercury.

* * * * *